_United States Patent_ [19]

Hompel et al.

[11] Patent Number: 5,220,826

[45] Date of Patent: Jun. 22, 1993

[54] METHOD AND APPARATUS FOR MEASURING MATERIALS FLOATING ON BODIES OF WATER

[76] Inventors: Michael T. Hompel, Am Sturmwald 40, D-4600 Dortmund 50; Helmut Klesper, Eintrachtstr. 48, D-4040 Neuss 1, both of Fed. Rep. of Germany

[21] Appl. No.: 613,486

[22] PCT Filed: Mar. 14, 1990

[86] PCT No.: PCT/EP90/00413

§ 371 Date: Oct. 30, 1990

§ 102(e) Date: Oct. 30, 1990

[87] PCT Pub. No.: WO90/11517

PCT Pub. Date: Oct. 4, 1990

[30] Foreign Application Priority Data

Mar. 22, 1989 [DE] Fed. Rep. of Germany ....... 3909342

[51] Int. Cl.[5] ............................................. G01N 29/02
[52] U.S. Cl. .................................... 73/61.49; 73/61.79
[58] Field of Search ................ 73/61.79, 61.49, 61.51, 73/61.43, 64.48, 170 A; 324/698, 699, 722

[56] References Cited

U.S. PATENT DOCUMENTS

| 3,336,799 | 8/1967 | Kermode | 73/170 A |
| 4,512,183 | 4/1985 | Alexander | 73/64.48 |

FOREIGN PATENT DOCUMENTS

| 2836972 | 3/1980 | Fed. Rep. of Germany. | |
| 678313 | 8/1979 | U.S.S.R. | 73/170 A |
| 1251007 | 8/1986 | U.S.S.R. | 73/170 A |
| 1283621 | 1/1987 | U.S.S.R. | 73/64.48 |

_Primary Examiner_—Hezron E. Williams
_Assistant Examiner_—Joseph W. Roskos
_Attorney, Agent, or Firm_—Anderson Kill Olick & Oshinsky

[57] ABSTRACT

A method and an apparatus for measuring materials of high viscosity floating on bodies of water are to provide a solution enabling a reliable monitoring of the water surface of standing and running bodies of water using simple means. This is achieved by means of the method in that the water surface of the body of water is excited by means of an oscillating device and in that the surface waves reflecting on the water surface are measured.

9 Claims, 3 Drawing Sheets

METHOD AND APPARATUS FOR MEASURING MATERIALS FLOATING ON BODIES OF WATER

The invention is directed to a method and an apparatus for measuring materials floating on bodies of water, which materials are highly viscous relative to water.

Such methods serve particularly for determining contamination such as oil films at the surface of bodies of water, e.g. in drainage ditches, rain reservoirs, etc. Thus, continuous optical methods are known for determining oil films, in which methods a light source radiates on the water surface and the light reflected by the water surface is measured in corresponding optical measuring devices such as photodiodes or television cameras. If an impurity, e.g. due to oil, occurs in the irradiated water surface, the composition of the reflected light changes and an alarm is then triggered by the measuring device. These measuring methods work relatively reliably, but because of the complicated optical devices they are very expensive and accordingly cost-intensive.

Further, discontinuous measuring methods are known in which mechanical samples are taken from time to time, whose optical characteristics are determined by means of measuring the reflection or absorption behavior or whose electrical characteristics are determined by means of determining the dielectric coefficient of the water surface. A disadvantage in these methods consists in that a costly mechanism is necessary for automatically carrying out the taking of samples, which involves a correspondingly high maintenance cost and high probability of failure. Moreover, such discontinuous methods are unsuitable for monitoring running bodies of water.

The present invention therefore has the object of providing a solution which enables a reliable monitoring of the water surface of standing and running bodies of water using simple means.

This object is met, according to the invention, with a method of the type described in the beginning in that the water surface of the body of water is excited by means of an oscillating device and in that the surface waves reflecting on the water surface are measured.

It is possible with this method to monitor the water surface of standing and running bodies of water in a simple manner without the need of complicated optical devices or the like. Characteristic surface waves occur at the water surface by means of exciting the water below the water surface and are correspondingly measured by means of a measuring device. When a material of high viscosity, such as oil, occurs on the water surface, the surface waves are damped, which is determined by the measuring device and converted into a corresponding warning signal or the like.

The invention advantageously provides that natural movements of the water surface are mechanically and/or electronically damped in the surface wave measurement. Such a damping is provided in particular when particularly mobile bodies of water are to be monitored.

It is especially advantageous if the body of water is excited to oscillate by means of sound waves. In this case, e.g. conventional underwater loudspeakers can be used as an oscillating device.

In order to meet the object proposed in the beginning the invention also provides an apparatus which comprises an oscillating device arranged on or under the water surface and a surface wave measuring device arranged at the assigned water surface. The composition of the water surface can be monitored with such an apparatus in a simple manner without the need of costly optical devices or the like.

It is particularly advantageous if the oscillating device and the surface wave measuring device are arranged so as to float under or on the water surface. With a changing water level, it is accordingly ensured that the oscillating device and the surface wave measuring device, respectively, remain in the same position relative to the water surface.

It is particularly advantageous if the oscillating device and the surface wave measuring device are arranged on reciprocal floats. It is accordingly ensured that the oscillating device and the measuring device remain in the same position relative to one another also when the water surface is not calm, so that no falsification of the measurements occurs as a result of natural movement of the water surface.

The invention further provides that the oscillating device is constructed as a watertight loudspeaker. Of course, other, particularly mechanical, systems capable of oscillation can also be used.

The surface wave measuring device can be formed by electrodes which are acted upon by current and are arranged in the area above the oscillating device so as to be immersed under the water surface. However, other dynamically operating displacement measuring devices, such as ultrasonic sensors or laser interferometers, can also be used.

When using electrodes as surface wave measuring device it is advantageously provided that the electrodes can be acted upon by alternating current and are connected to an evaluating device via a rectifier or electrical filters. Due to the application of alternating current, an electrolysis at the electrode wires is prevented to a great extent, the received measurement signal is freed from disturbing influences by means of the subsequently arranged electronic devices and correspondingly fed to the evaluating device which sends a disturbance signal or the like when impurities occur at the water surface.

The invention is explained in more detail in the following by way of example with the aid of the drawing.

Figure 1:
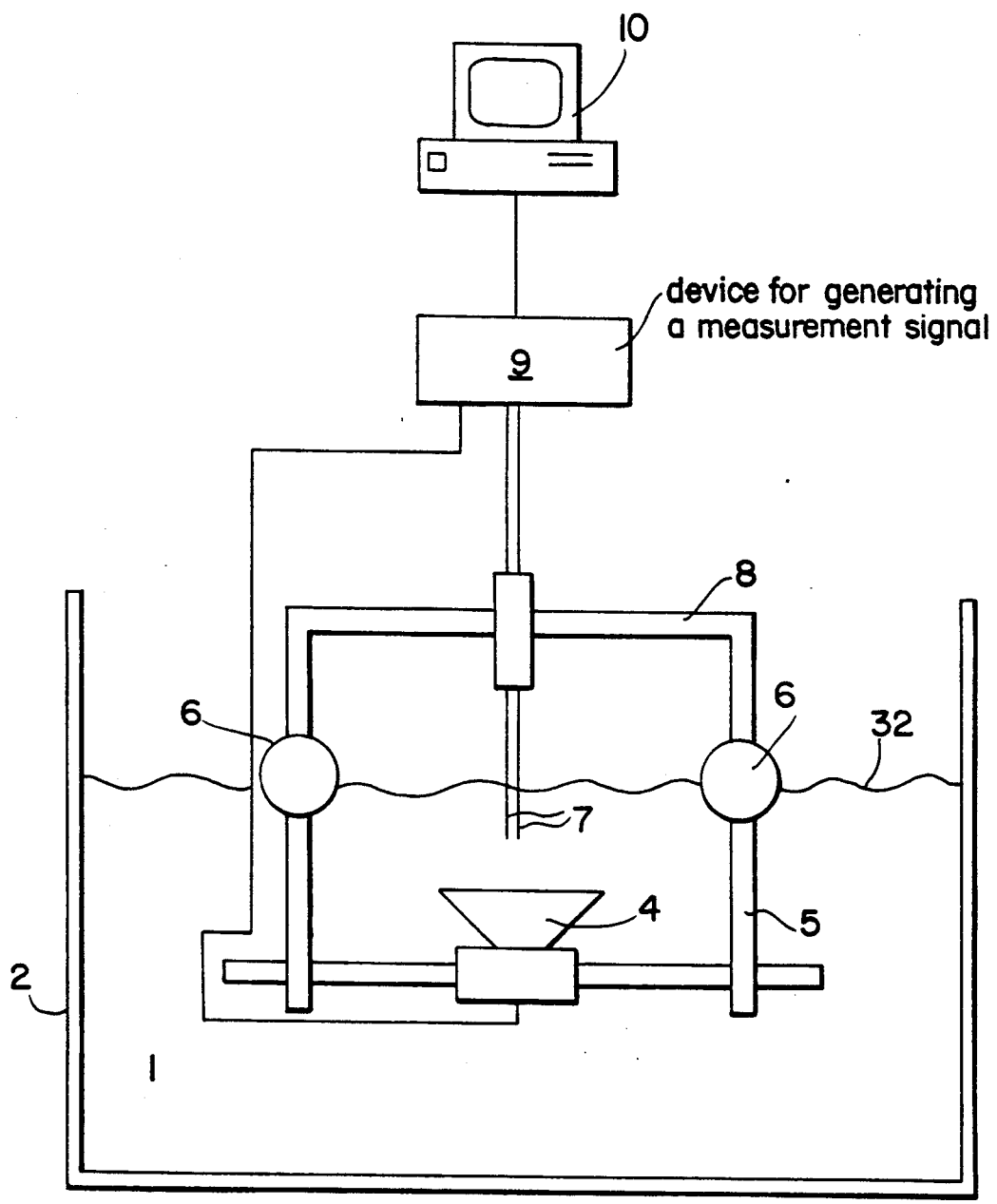
FIG. 1 shows a schematic view of an apparatus for implementing the method according to the invention.

A container 2 filled with water 1 is shown only by way of example in the drawing, wherein the water surface is designated by 3. The container 2 can represent e.g. a drainage ditch, a rain reservoir or also a river bed or the like, i.e. the water 1 in the container can be either a standing or running body of water.

An oscillating device constructed as a watertight underwater loudspeaker 4 is fastened by means of fastening elements 5 on two floats 6 floating on the water surface 3 in such a way that it is arranged below the water surface 3. Further, two platinum electrodes 7 are provided which serve as surface wave measurement device and are likewise arranged on the floats 6 by means of additional fastening elements 8 and dip below the water surface 3 in the area above the oscillating device 4.

Figure 2:
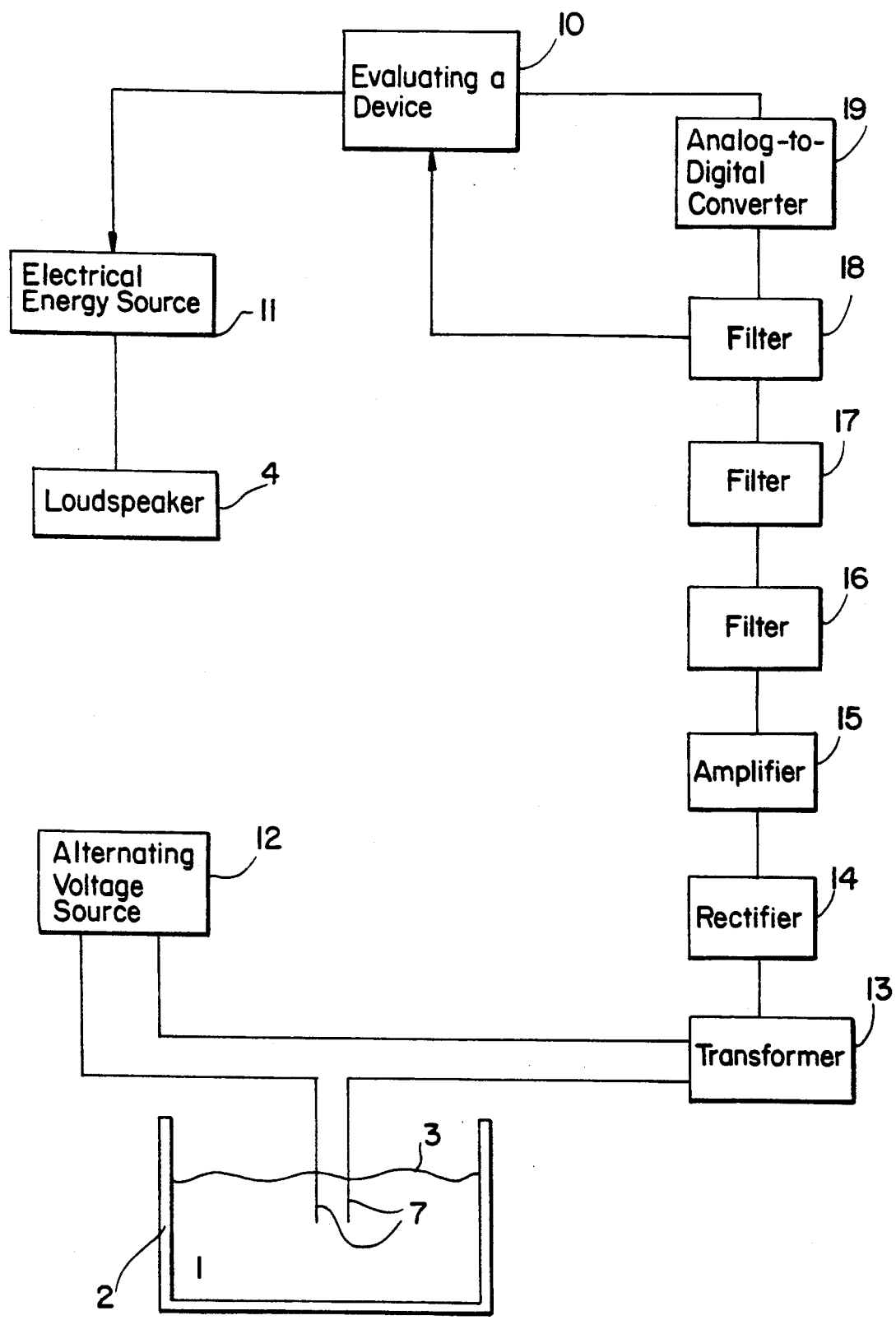
FIG. 2 shows the apparatus according to FIG. 1 with evaluating circuit.

The underwater loudspeaker 4 and the electrodes 7 are connected to an electronic device 9 with assigned evaluating device 10 whose basic construction is shown in FIG. 2.

The loudspeaker 4, whose diaphragm is arranged parallel to the water surface 3, is continuously provided with electrical energy at a constant frequency and output by an electrical energy source 11 of the electrical device 9, so that the diaphragm of the loudspeaker 4 is continuously excited to oscillation. The emitted sound waves propagate correspondingly in the direction of the water surface 3, where they produce surface waves on the water surface 3. As a result of this surface wave formation, the platinum electrodes 7 dip into the water to various depths as a function of the time, so that the electrical resistance between the electrodes 7 changes in a correspondingly proportional manner. In order to measure this resistance, an alternating voltage source 12 is used, so that an unwanted electrolysis is extensively prevented from taking place at the electrodes.

The alternating voltage proportional to the surface wave movement is received by a transformer 13 and rectified in a rectifier 14 in order to suppress the alternating frequency of the alternating voltage source 12. The rectified signal 14 is amplified in an amplifier 15 and filtered in an electrical filter system 16, 17, 18 (low-pass and high-pass filters) in such a way that it is freed from all disturbances.

The signals prepared by the electronic device 9 are read into and correspondingly processed in the evaluating device 10, particularly a computer, via an analog-to-digital converter 19.

Figure 3:
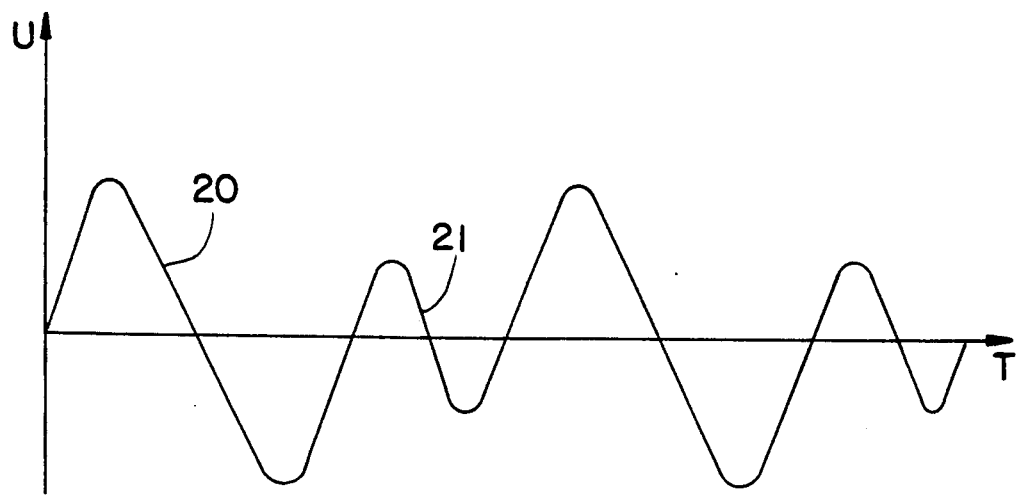
FIG. 3 shows a voltage-time diagram for pure water.

FIG. 3 shows a typical output signal for pure water which substantially comprises a carrier wave 20 and a wave of half frequency 21.

Figure 4:
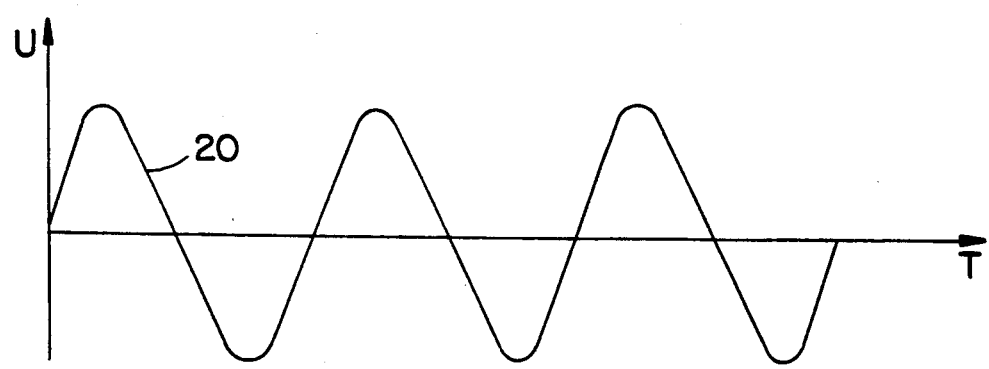
FIG. 4 shows a voltage-time diagram for water contaminated with oil.

If a highly viscous material such as oil occurs at the respective water surface, the surface wave movement is sharply damped, which leads to another output signal which is shown in FIG. 4 and clearly differs from the signal shown in FIG. 3. In particular, it can be seen that the wave of half frequency 21 is completely damped. If such a disturbance is determined by the evaluating device 10, corresponding warning devices or the like are automatically actuated.

Movements of the floats 6 due to external water waves are damped by means of the electrical filter system 16, 17, 18 as well as by inner filters of the evaluating device 10, so that they have practically no significance.

Naturally, the invention is not limited to the embodiment examples shown in the drawing; other constructions are also possible without departing from the basic idea. For example, other systems capable of oscillation can also be used as an oscillating device and also other dynamically operating displacement measuring devices, such as ultrasonic sensors or laser interferometers, can be used as a surface wave measuring device.

We claim:

1. Method for measuring materials floating on bodies of water, which materials are highly viscous relative to water, characterized in that a water surface of a body of water is excited by means of an oscillating device; that the surface waves reflecting on the water surface are measured; and that the material movements of the water surface are mechanically and/or electronically damped during the surface wave measurement.

2. Method for measuring materials floating on bodies of water, which materials are highly viscous relative to water, characterized in that an unconfined water surface of a body of water is excited by means of an oscillating device; that the surface waves relfecting on the water surface are measured; and that the reflecting surface waves are compared with stored reference surface waves of non-contaminated water.

3. Method according to claim 2, characterized in that the body of water is excited to oscillation by means of sound waves.

4. An apparatus for measuring materials floating on bodies of water, which materials are highly viscous relative to water, characterized by comprising an oscillating device to be arranged on or below an unconfined water surface of a body of water for exciting the water surface; a measurement device to be arranged on the water surface for measuring surface wave reflecting on the water surface; and an evaluating device for comparing the reflecting surface waves with stored reference surface waves of non-contaminated water.

5. Apparatus according to claim 4, characterized in that the oscillating device (4) and the surface wave measuring device (7) are arranged so as to float under or on the water surface (3).

6. Apparatus according to claim 4, characterized in that the oscillating device (4) and the surface wave measuring device (7) are arranged on reciprocal floats (6).

7. Apparatus according to claim 4, characterized in that the oscillating device (4) is constructed as a watertight loudspeaker.

8. Apparatus according to claim 4, characterized in that the surface wave measuring device (7) is formed by electrodes which are acted upon with current and are arranged in the area above the oscillating device (4) so as to be immersed below the water surface (3).

9. Apparatus according to claim 8, characterized in that the electrodes (7) can be acted upon by alternating current and are connected to an evaluating device (10) via a rectifier (14) and electrical filters (16, 17, 18).

* * * * *